United States Patent [19]

Wadsö et al.

[11] Patent Number: 4,492,480

[45] Date of Patent: Jan. 8, 1985

[54] PROBE FOR USE IN A MICROCALORIMETER

[76] Inventors: Ingemar Wadsö, Bläckhornsvägen 6, S-222 67 Lund; Jaak Suurkuusk; Robert L. Taylor, both of Gränsvägen 21, S-175 46 Järfälla, all of Sweden

[21] Appl. No.: 594,414

[22] Filed: Mar. 28, 1984

Related U.S. Application Data

[63] Continuation of Ser. No. 349,768, Feb. 18, 1982, abandoned.

[30] Foreign Application Priority Data

Feb. 26, 1981 [SE] Sweden ............................ 8101245

[51] Int. Cl.³ ............... G01K 17/00; G01N 25/20
[52] U.S. Cl. ............................. 374/33; 165/169; 374/12; 435/291
[58] Field of Search .............. 374/31, 33, 10, 12, 374/13, 29; 422/51; 436/147; 435/251; 165/164, 169

[56] References Cited

U.S. PATENT DOCUMENTS

| | | | |
|---|---|---|---|
| 2,440,245 | 4/1948 | Chevigny | 165/169 |
| 3,059,471 | 10/1962 | Calvet | 374/33 |
| 3,148,532 | 9/1964 | Broerman | 73/23.1 |
| 3,273,968 | 9/1966 | Banzinger | 374/31 X |
| 3,314,288 | 4/1967 | Sherwin | 374/13 |
| 3,765,237 | 10/1973 | Blackmer et al. | 374/31 |
| 3,798,003 | 3/1974 | Ensley et al. | 422/51 |
| 3,841,155 | 10/1974 | Koehler et al. | 374/33 |
| 3,972,681 | 8/1976 | Clack et al. | 422/51 |
| 4,054,056 | 10/1977 | Wegstedt et al. | 422/51 X |

FOREIGN PATENT DOCUMENTS

| | | | |
|---|---|---|---|
| 307683 | 4/1969 | Sweden | 435/291 |
| 329025 | 1/1971 | Sweden | 435/291 |
| 610007 | 5/1978 | U.S.S.R. | 374/10 |

OTHER PUBLICATIONS

"Bioactivity Monitor" LKB Brochure, 6 pages, No. 2277-00B-DBE, 10/1982.

"Principles of Heat Flow Monitoring" LKB Brochure, pp. 7-15, 10/1982.

Primary Examiner—Daniel M. Yasich
Attorney, Agent, or Firm—Fisher, Christen & Sabol

[57] ABSTRACT

Probe (1) to be used in a microcalorimeter for various types of heat measurements. The probe having a good thermal contact with thermodetectors (5,6) used in the calorimeter. The probe is designed as a substantially cylindrical hollow body has at least one outer surface (4, 11) which is in contact with the thermodetectors. The outer surface of the probe is provided with a helix groove (2) in which a tube (3) for supplying the continuous flows is arranged in good thermal contact with the probe. The cavity (10) of the body is used for the introduction of the ampoules (9).

3 Claims, 1 Drawing Figure

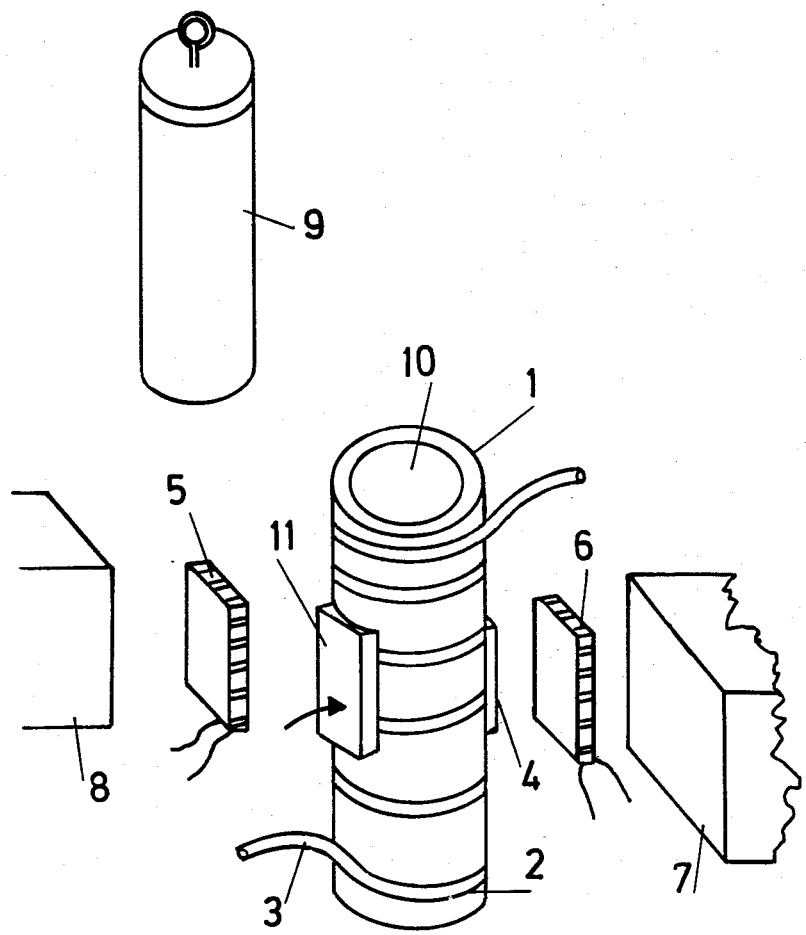

PROBE FOR USE IN A MICROCALORIMETER

This application is a continuation of application Ser. No. 349,768, filed Feb. 18, 1982, abandoned.

BACKGROUND OF THE INVENTION

1. Field of the Invention

The present invention refers to a probe for use in a microcalorimeter in which various types of heat measurements are carried out, such as the heat development of continuous flows and, the heat development from closed ampoules or ampoules to which during measurement some further medium is added, whereby the probe is arranged in thermal contact with the thermodetectors used in the calorimeter.

2. Prior Art

Microcalorimetry is a universal method for quantifying different types of chemicals and above all biochemical processes by measuring the heat development of these processes. A number of different microcalorimetric principles are known an example is the thermoelement heat leakage principle described for instance in the Swedish Pat. Nos. 307 683 and 329 025.

In a microcalorimeter one is interested in carrying out different types of heat measurements such as the heat development in continuous flows of a medium or a mixture of several media or the heat development of solid or fluid objects under static conditions, whereby the objects are arranged in closed ampoules. A further application is the so-called perfusion experiment, where a gas or a liquid is supplied for instance to a living biological cell system enclosed in a reaction vessel. In the microcalorimeters known per se the change between these different types of experiments has implied that the probe of the calorimeter has been exchanged completely which is a relatively time-consuming operation.

BROAD DESCRIPTION OF THE INVENTION

It is an object of the present invention to provide a probe by means of which the calorimeter can be modified in a simple way for carrying out the desired type of measuring.

The invention involves a probe for use in a microcalorimeter in which various types of heat measurements are carried out, such as, the heat development of continuous flows, and/or the heat dvelopment from closed ampoules or ampoules to which during measurement some further medium is added, whereby the probe is arranged in thermal contact with the thermodetectors used in the calorimeter. The probe designed as a substantially cylindrical hollow body having at least one outer surface, which is in contact with the thermodetector whereby the outer surface of the body is provided with a helix groove provided with a tube through which the continuous flows could be supplied. The tube has a good thermal contact with the body. The cavity of the hollow body is used for the introduction of the ampoules. The flat surfaces can be arranged on one part of the outer envelope surface of the cylinder. The cylinder can be provided with two opposite flat surfaces.

BRIEF DESCRIPTION OF THE DRAWING

The probe according to the invention will now be described in detail, reference being made to the attached drawing which schematically shows one embodiment of the invention.

DETAILED DESCRIPTION OF THE INVENTION

In the drawing, reference 1 denotes a probe made from a material of good heat conductivity such as aluminum or silver. The probe is designed as a cylindrical cavity and is provided with helix groove 2 around its outer envelope surface. In the groove, tube 3 is arranged having good thermal contact with the probe. The tube is intended to be used in flow measurements, i.e., the heat development in continuous flows of a medium or a mixture of several media. In cavity 10 of the probe, ampoule 9 can be introduced when measuring the heat development from solid or fluid objects under static conditions or at so called perfusion experiments in which the ampoule is supplied with a gas or a liquid. The probe is provided with two flat surfaces 4, 11 which are brought into good thermal contact with thermodetectors 5, 6 which according to the embodiment consist of so called Peltier elements for measuring the heat flow from the probe. The Peltier elements are in contact with each one of heat sinks 7, 8—the sinks having an eternal heat capacity.

The probe shown in the drawing is suitably manufactured by starting up from a metal cylinder having an outer diameter which is bigger than the distance between flat surfaces 4 and 11. In this surface groove 2 is milled to a suitable depth whereafter the cylinder is turned in a lathe outside of flat surfaces 4 and 11 and cavity 10 is drilled. Flat surfaces 4 and 11 will then form one piece with the cylinder which is essential in order to obtain a suitable heat conductivity.

We claim:

1. A device for use in a microcalorimeter, comprising a hollow tubular body adapted to receive an article which contains at least one material to be thermally tested therein; said hollow tubular body being further adapted to conduct heat generated by the article received therein;

a fluid conduit adapted to conduct heat;

said hollow tubular body having a continuous helical groove about its periphery, said helical groove being adapted to receive said fluid conduit therein;

said fluid conduit being adapted to receive a heat-generating fluid flowing therethrough;

first and second heat-conducting members fixedly attached to the outer periphery of said hollow tubular body, and first and second heat-conducting members being adapted to conduct heat from said hollow tubular body and said fluid conduit; each of said first and second heat-conducting members having a generally flat surface thereon;

a first and second Peltier thermocouple having one side thereof in thermal contact with respective ones of said generally flat surfaces of said first and second heat-conducting members;

said first and second Peltier thermocouples each having another side in thermal contact with a heat sink, each said heat sink having sufficient heat capacity so as to be adapted to remain at a substantially constant temperature while heat is being conducted across said first and second Peltier thermocouples;

heat generated within said hollow tubular body and said fluid conduit being conducted to said heat sinks;

whereby heat generated within said hollow tubular body and said fluid conduit, passing across said first and second heat-conducting members and passing across said first and second Peltier thermocouples, is measureable by said first and second Peltier thermocouples.

2. A device as claimed in claim 1, wherein at least a portion of the fluid conduit passes entirely between said hollow tubular body and said first heat-conducting member;

whereby heat from said fluid conduit is effectively conducted to said first Peltier thermocouple by said first heat-conducting member.

3. A device as claimed in claim 2, wherein at least a portion of the fluid conduit passes entirely between said hollow tubular body and said second heat-conducting member;

wherein heat from said fluid conduit is effectively conducted to said second Peltier thermocouple by said second heat-conducting member.

* * * * *